United States Patent
Frankie

(10) Patent No.: US 6,309,407 B1
(45) Date of Patent: Oct. 30, 2001

(54) PAN SELF UNIT PORTABLE ALTERNATOR NERVE STIMULATOR

(76) Inventor: Edmun Lee Frankie, P.O. Box 155, 735 W. Main, Homer, LA (US) 71040

(*) Notice: Subject to any disclaimer, the term of this patent is extended or adjusted under 35 U.S.C. 154(b) by 0 days.

(21) Appl. No.: 09/517,703

(22) Filed: Mar. 2, 2000

(51) Int. Cl.$^7$ ....................................... A61N 1/08
(52) U.S. Cl. ............................................. 607/46
(58) Field of Search .................. 607/115, 44, 46, 607/48, 150; 322/1

(56) References Cited

U.S. PATENT DOCUMENTS 5,405,376 * 4/1995 Mulier et al. .

* cited by examiner

Primary Examiner—Mark Bockelman

(57) ABSTRACT

Starting with a hand or foot-pumped alternating current flashlight, the reflector, bulb, lens and lens cap are removed. A one or more stage step-up miniature transformer of at least 1 to 5 ratio is mounted in the hole where the said parts are removed. The low voltage side of the transformer is connected to the wires from the alternator, and the high voltage side of the transformer is connected to two about six foot interconnected wires, which transfer power to the phono plug. (If a multi-stage transformer is used, the low voltage is connected as said, and the high voltage side is connected through a switch. One wire from the phono plug is connected to the switch. The electrical switch can change the electrical current in stages.) The wires are about six feet long and are fed through a small hole in the cap and the cap attached to the alternator body. The ends of the wires are fed through a hole in the handle of about a three-section telescoping wand and one connected to an L-shaped phono plug. The A penetrating lubricant should be placed on the part of the body to receive the current from the phono plug. The wand can be extended so the user can reach any part of the body. While pumping the alternator, the wand is used in a circular motion around the painful area.

14 Claims, 1 Drawing Sheet

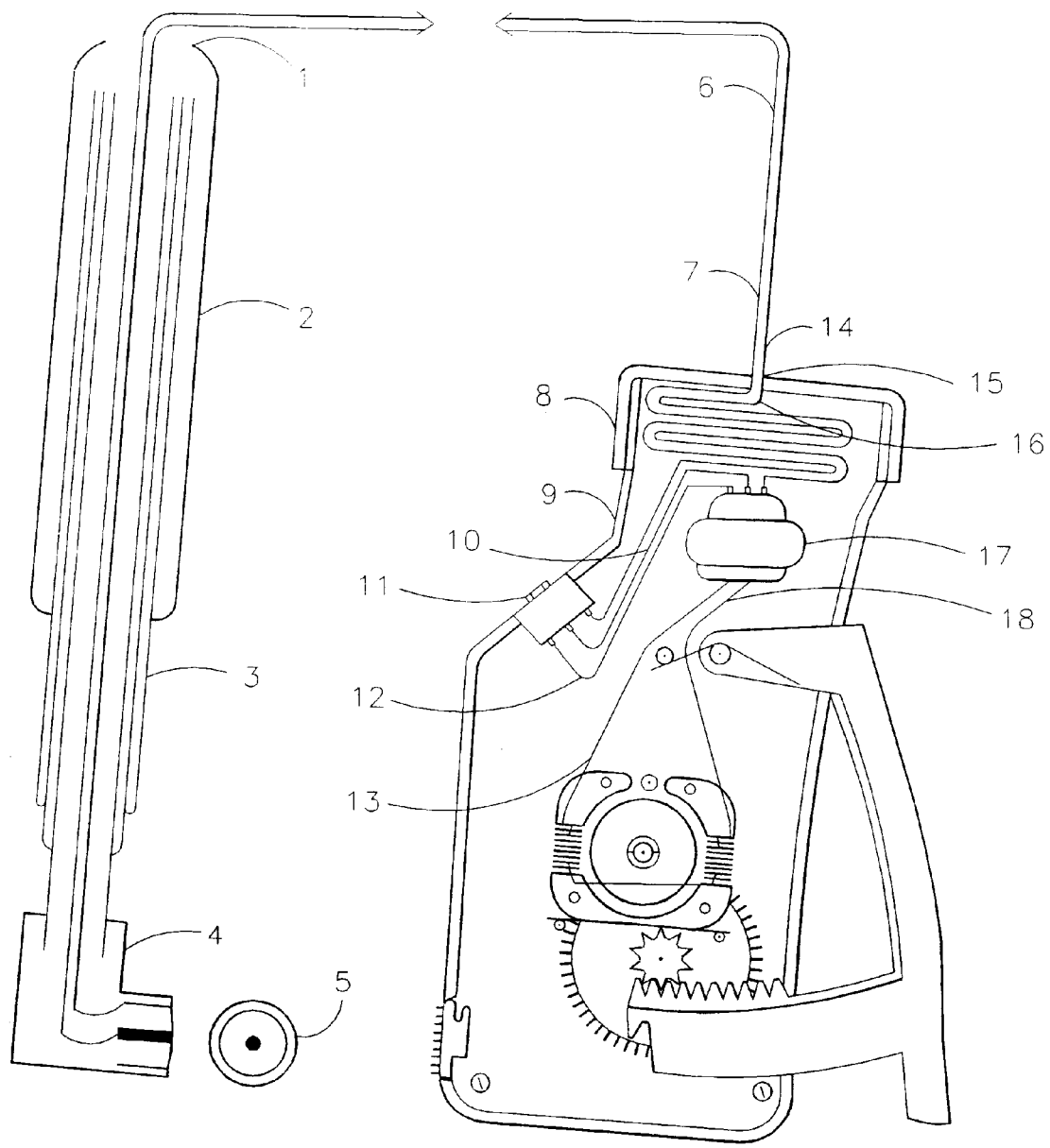

PAN SELF UNIT PORTABLE ALTERNATOR NERVE STIMULATOR

BACKGROUND OF THE INVENTION

The PAN SELF Unit could be used in the medical field as an electrical nerve stimulator and/or for pain control under U.S. Patent Classification Definition D24 Medical and Laboratory Equipment—231 Miscellaneous (70).

The advantages of the PAN SELF UNIT are: 1. Small in size, 2. Produces its own alternating electrical current, 3. Safe to be used around water (although the mechanism can be harmed by submersing it in water), 4. The user can reach any part of their body without outside help, 5. The user has control of the electrical flow by pumping slow or fast on the band/foot pump.

BRIEF SUMMARY OF THE INVENTION

This invention will stimulate nerves and in many cases control pain in the body by blocking pain impulses and it will cause the body to release endorphins, which control pain perception. The amount of voltage released is in proportion to the speed at which a person pumps the alternator. This device can be pumped by squeezing and releasing pressure so the pump handle springs can return it to the position to be pumped again. The same result can be obtained by pressing on the handle with the foot and then releasing it. This allows the user to regulate the voltage to a tolerable amount.

1. Circumstances of Conception.

One day in 1979 I was using an electric drill and grounded out my arm on a cooking Range. I was held there by the electrical current until the breaker switched off. I noticed that for several weeks following, I had no pain in my hands, fingers, and wrists, that were usually painful from Osteoarthritis. This began my search for a safe, portable electrical stimulation device that could duplicate the electrical stimulation I had received. I later found out that one is used by physical therapists in hospitals. The device rolls from room to room, and plugs into a 110 volt outlet. It is too large for my plans. Another is the TENS unit, which has to be connected to the body with electrodes and is also bulky. I even traveled to Hot Springs, Ark., to go through the museum where some of the first electrical stimulation machines were developed and used along with the spring baths. These stimulators were also too bulky and antiquated.

In the late 1940s I had seen a hand-operated flashlight that took no batteries. Its energy was created by hand-pumping a grip on the flashlight. This pumping-motion moved a curved-toothed stem at one end of the grip into the flashlight. The teeth of the grip would come in contact with a gear on the alternator's armature, causing the armature to spin, thereby creating the electrical power.

In about May of 1994, I ordered some Dynamo Flashlights made in China These received their electrical current by squeezing a spring-loaded handle, as described above. I discovered that this device produced alternative current, which would allow me to connect a step-up Miniature Transformer to increase the voltage. In September of 1994I produced my fist alternator stimulator. In 1997, I discovered that China had another flashlight on the market, and that Russia had a similar alternator flashlight, that worked the same way, and could have the volts increased by use of a small transformer. Either of these can have the voltage regulated according to the speed at which it is pumped. I did not find any patent markings on any of the three flashlights mentioned above. I did a patent search on the three flashlights at Rice University's Fondren Library in Houston, Tex., and found nothing that came close to my invention.

2. Purposes and advantages of the invention

This device relieves pain by producing alternating current to stimulate nerves in and around muscles, joints, tendons, nerves, ligaments, and bones of the body. Advantages of the PAN SELF Unit are: a) It uses no batteries or outside electrical current, b) It is small enough to fit in a person's pocket or purse, c) It can be used in remote areas where no electricity is available, d) It can also be used in emergency situations, when there is a power outage, e) It is safe to use around water including the bathtub, but should not be submerged, f) It is safe for a laypeson to use, g) The PAN SELF Unit will be cost-effective for the average person.

1. A sufficient-size whole is disposed at the bottom of the telescoping wand so that the telescoping wand can be extended or retracted without harming the wires.
2. Insulated Handle.
3. At least three-section slidable telescoping wand.
4. "L"-shaped phono plug.
5. Front view of said phono plug.
6. Twin-irrulated contiguous wire, about 6 feet (1.8288 meters) long.
7. Insulated Wire from switch to "L"-shaped phono plug.
8. Cut-away view of housing cap.
9. Cut-away view of housing.
10. Insulated wire from transformer low voltage to switch
11. Switch to regulate voltage from Low to High.
12. Insulated wire from transformer high voltage to switch
13. Wire from alternator to transformer.
14. Insulated wire from transformer to "L"-shaped phono plug.
15. Circular hole in center of cup for twin-insulated wires to come through.
16. Twin insulated wire tied in a knot so it won't pull through hole in cap.
17. About a two-stage step-up transformer.
18. Wire from alternator to transformer.

DETAILED DESCRIPTION OF THE INVENTION

This invention is manufactured from a hand/foot-pumped alternator flashlight which had the lens cap, reflector, and bulb removed. This alternator produces from 0–14 volts depending on the speed it is pumped. A solid cap with a small hole in the center of the cap is used in place of the lens cap.

A miniature, at least single-stage transformer, with at least a one to five ratio is placed in the housing with its low voltage end connected to the wires leading to the alternator. The high volt wires are connected to the insulated dual wires leading into the cap. (The wires leading into the cap have about 3 inches of wire inside the cap, with a knot tied in the end so that the wire can't pull through the hole in the cap and pull the connection loose.)

When a multi-stage miniature transformer is used the low voltage wires are connected to the wires leading to the alternator. On the high voltage side, one wire is connected to one of the wires leading into the cap. Any other wires from said transformer are connected to a miniature switch which changes voltage to different levels. The second wire that leads in from the cap connects to the miniature switch All connections are soldered or crimped together and insulated with tape or liquid rubber. The cap is securely fastened to the unit.

The two wires that extend outside the cap are about six feet in length. The end of the two insulated wires are mounted through the handle of a three-section telescoping wand that will measure about 6.75 inches to about 15 inches and is connected to an L-shaped phono plug that has a modified center electrode, so its surface will be almost the same level as the outside metal surface. This telescoping wand has a hole in the end of the handle large enough to let the wire slide freely as the wand is lengthened and shortened. By using said device along with the length of wire the user should be able to pump the alternator by band or by foot, and reach any part of their body with the stimulant produced.

The wand has an insulated handle measuring about 3.5 inches.

It is recommended that for best results, the user apply some skin-penetrating lotion or water on the area of the body to be stimulated before they use the PAN SELF Unit.

The stimulator should be used at its lowest volts when starting and work up to a level that is well tolerated by the person using it.

To operate the PAN SELF Umt, place the handle of the wand in one hand and Extend the wand to the length needed to reach the part of the body to be worked on. Place water or a skin-penetrating gel or lotion on the area to be worked on. Pump the alternator, and slowly, in a circular motion, move the end of the phono plug around the area being treated. An area that is more sensitive may need more time spent on it with less voltage used for the sake of tolerance. As the user becomes used to the electrical tingle, the power can be increased for deeper penetration.

What is claimed is:

1. An electrical device comprising:

A portable hand or foot pump operated electrical generator serving as an electrical source of power, a least a single stage step-up, miniature transformer, arranged so as to receive a first voltage from the portable pump and deliver a second higher voltage to two insulated conductors electrically connected to said transformer, a telescoping wand having two electrical receptacles near one end on the wand and wherein the insulated electrical conductors are in electrical communication with said two electrical receptacles.

2. The electrical device of claim 1 wherein the output of the hand or footpump generator is up to 14 volts of alternating current.

3. The electrical device of claim 2 where in the voltage generated by the foot or hand pump generator may be varied by pumping the hand or foot pump at different rates.

4. The electrical device of claim 2 wherein the transformer is a 1 to 5 step-up transformer which may produce up to 70 volts of safe alternating current.

5. The electrical device of claim 2 wherein the two insulated conductors are interconnected and about 6 feet in length.

6. The electrical device of claim 5 where in the insulated conductors are connected to the transformer at one end and have a knot tied therein about 3 inched from the transformer, and are fed through a small center hole in a cap on a housing that encloses the power source and on to the wand.

7. The electrical device of claim 6 wherein the wand has a handle with an opening at its end which permits the two insulated conductors to slide smoothly therein as the telescoping part of the wand is extended and retracted.

8. The electrical device of claim 7 wherein the two insulated conductors extend through said wand and are connected to an L-shaped phone plug that has the center electrode modified to be about even with the outside electrode and serving as the two electrical receptacles.

9. The electrical device of claim 8 wherein the combination of the about 20 foot insulated conductors, the phono plug, and the telescoping wand in an extended position can reach any part of the user's body for the delivery the alternating current to a treatment site.

10. The electrical device of claim 1 wherein the at least a single stage, miniature step-up transformer is a multi-stage transformer, and where in at least one conductor on the higher voltage side of the transformer is connected to one of the insulated conductors that lead to a phonoplug and at least a second conductor leading from the transformer is electrically connected to a miniature switch which in turn is connected to the other insulated wire.

11. The electrical device of claim 10 wherein the transformer is a split-phase transformer which can develop up to 35 volts on the low phase and 70 volts on the high phase.

12. The electrical device of claim 10 wherein the switch permits switching from a low voltage of about 35 volts to a high voltage of about 70 volts.

13. The electrical device of claim 10 wherein the two electrical conductors are about six feet long.

14. The electrical device of claim 13 wherein one of the insulated conductors has one lead connected to a miniature switch and one lead connected to the transformer with a knot tied therein about 3 inches from the transformer and the conductor is fed through a small hole centered in a cap of a power source housing, then onto the wand.

* * * * *